Figure 1:
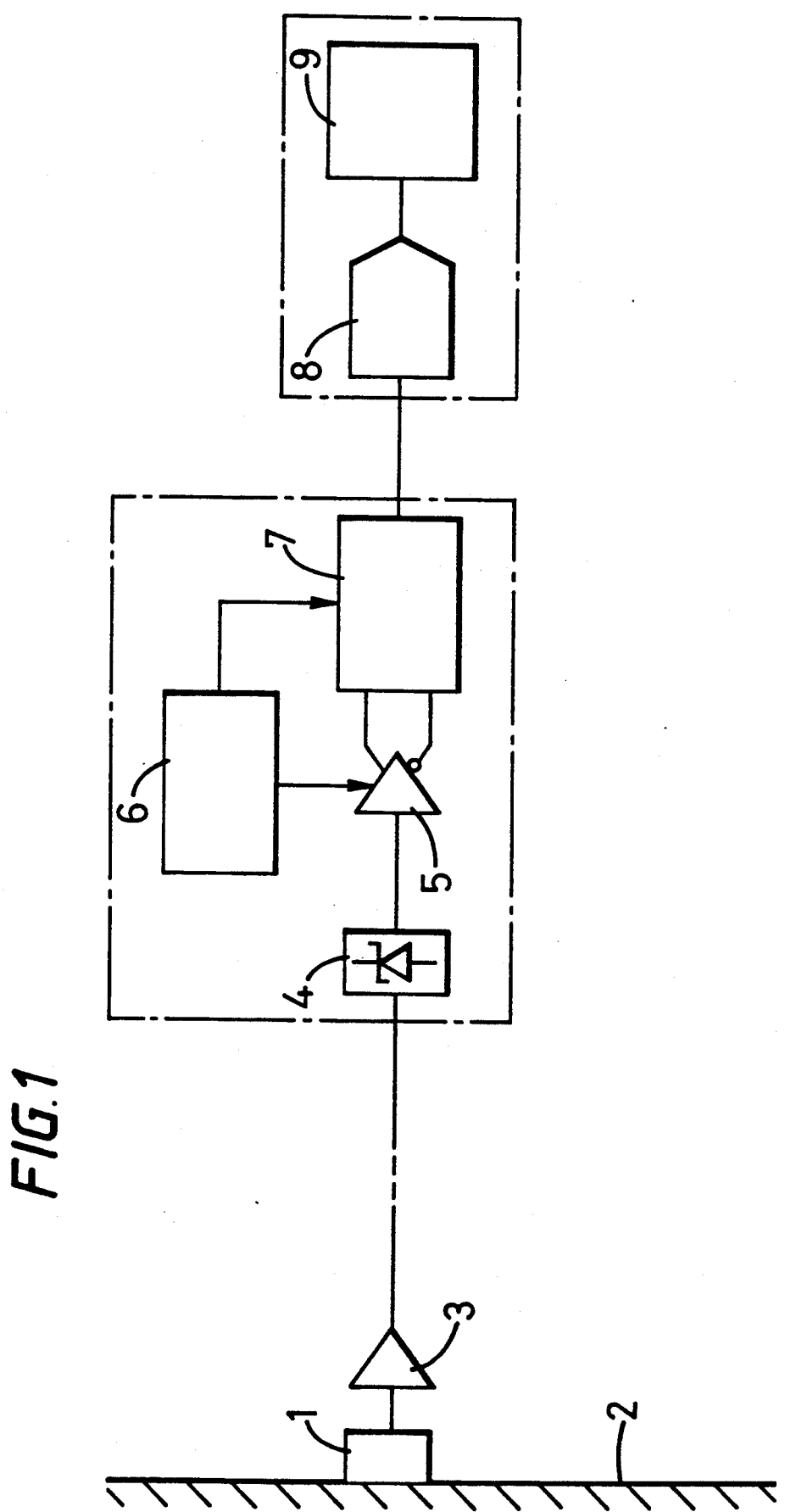

United States Patent [19]

Belchamber et al.

[11] Patent Number: 5,148,405
[45] Date of Patent: Sep. 15, 1992

[54] METHOD FOR MONITORING ACOUSTIC EMISSIONS

[75] Inventors: Ronald M. Belchamber, Berkshire; Derek Brister; Michael P. Collins, both of Middlesex; John Hill, Surrey, all of United Kingdom; Robert Watkins, Leidschendam, Netherlands; Douglas G. Wood, Berkshire, England

[73] Assignee: The British Petroleum Company p.l.c., London, England

[21] Appl. No.: 833,572

[22] Filed: Feb. 10, 1992

Related U.S. Application Data

[63] Continuation of Ser. No. 716,439, Jun. 17, 1991, abandoned.

[30] Foreign Application Priority Data

Jun. 27, 1991 [GB] United Kingdom ............... 9014251

[51] Int. Cl.$^5$ ........................................... G01N 29/02
[52] U.S. Cl. .................................... 367/13; 73/861.18
[58] Field of Search ........................... 367/13, 89, 127; 73/861.18, 861.27, 861.41

[56] References Cited

U.S. PATENT DOCUMENTS 4,628,725 12/1986 Gouilloud et al. ............... 73/861.27

FOREIGN PATENT DOCUMENTS 10104004 3/1984 European Pat. Off. .
2140560 11/1984 United Kingdom .
89/05974 4/1989 World Int. Prop. O. .

OTHER PUBLICATIONS

Control and Instrumentation, Feb. 1989, Roger Baker "Multi-Phase Flow Moves On," pp. 35 & 37.

Primary Examiner—Daniel T. Pihulic
Attorney, Agent, or Firm—Larry W. Evans; Dave J. Untener; Teresan W. Gilbert

[57] ABSTRACT

A non-intrusive method for the determination of characteristics of slug flow in a multiphase flow pipeline comprising the steps of: detecting the acoustic emissions from the pipeline in the ultrasonic frequency range by means of at least one sound transducer, the output from which is an analogue electrical signal, converting the analogue signal to a digital signal, and analyzing the digital signal to determine the characteristics of the slug flow.

The characteristics of slug flow which may be determined include distinguishing slug flow from wave flow, the frequency of slugging and the velocity and length of slugs. The method is particularly suitable for studying multiphase flow comprising oil, gas and water.

8 Claims, 4 Drawing Sheets

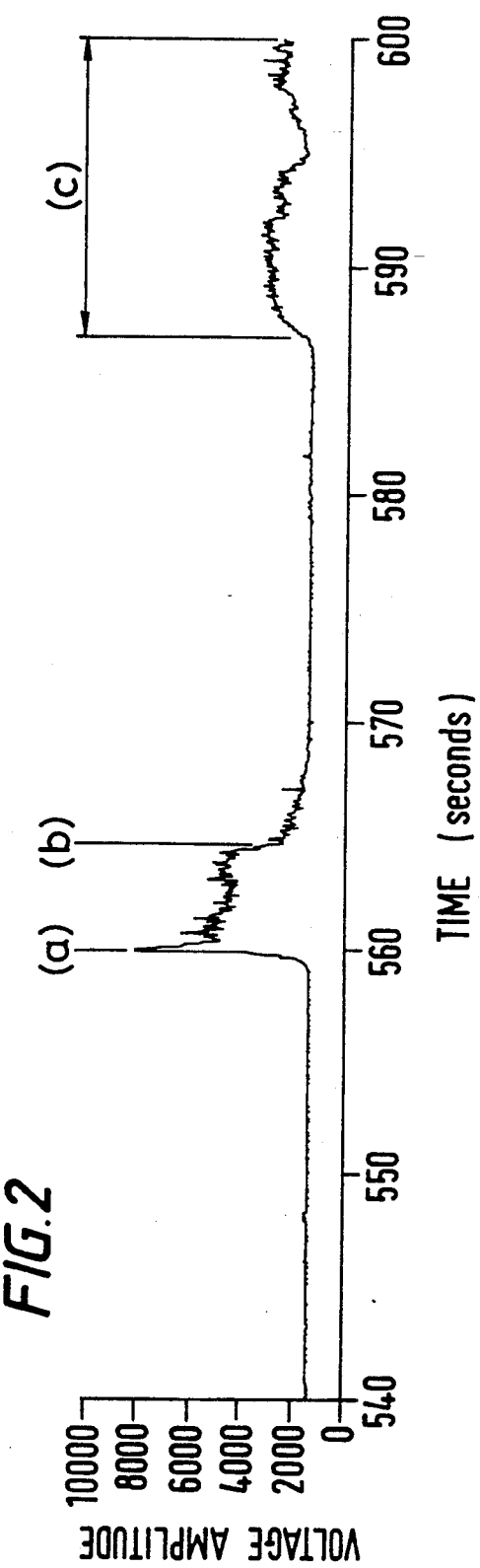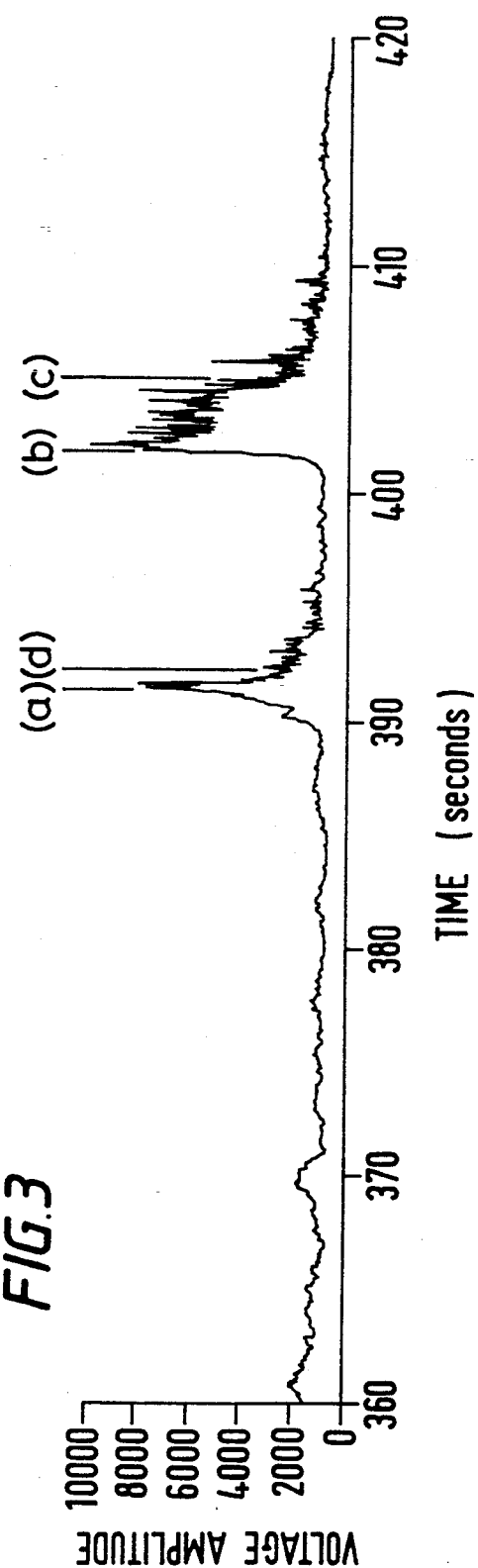

METHOD FOR MONITORING ACOUSTIC EMISSIONS

This is a continuation of co-pending application Ser. No. 07/716,439 filed on Jun. 17, 1991 now abandoned.

This invention relates to a method for monitoring multiphase flow in a pipeline by analysing acoustic emissions and in particular to a method for monitoring slug flow.

In the production of oil and gas unseparated reservoir fluids may be transported significant distances by pipeline.

In order to efficiently design and operate suitable pipelines for transporting oil and gas it is important that a thorough understanding of the behaviour of multiphase flow in pipelines, and on its resultant effects on processing facilities, is obtained.

One phenomenon occurring in a multiphase pipeline which can have a significant influence on both the operation of process plants and the mechanical construction of pipelines is slug flow.

Slug flow may be observed in a multiphase pipeline for a number of reasons.

Slugs may form in the wellbore and continue into the pipeline if there is no manifolding or choking at the wellhead.

Alternatively if the flow is initially well mixed at the start of the pipeline the fluids may initially separate out into a stratified wavy flow due to gravity. For certain conditions unstable waves may grow on the gas/liquid interface which eventually bridge the pipe and form slugs.

Slugs may also be formed due to the coalescence of bubbles, in particular where there is a low free gas/liquid ratio at the start of a line. As the pressure decreases along the line the existing gas expands and further gas comes out of solution. Bubbles of gas increase in size and then coalesce to form gas plugs which separate the liquid into slugs.

Slugs may also be formed due to changes in the pipeline terrain.

The occurance of slug flow leads to large variations in the gas and oil flowrates entering the downstream separator resulting in possible shutdown. Increased pipeline corrosion and mechanical damage to pipeline connections and supports can also be caused by slug flow.

It is important therefore to be able to detect slug flow and where it exists to obtain information on the slug flow characteristics such as the frequency, velocity and length of the slugs.

Information about the characteristics are required for example to size the separation equipment correctly and to design the piping supports.

Several methods have been used to study slug flow including gamma-ray densitometry but this is both expensive and also has safety and weight implications.

We have now found that by monitoring acoustic emissions, in the ultrasonic frequency range, from a multiphase flow pipeline the presence and characteristics of slugs may be detected.

Thus according to the present invention there is provided a non-intrusive method for the determination of characteristics of slug flow in a multiphase flow pipeline which method comprises the steps of (a) detecting the acoustic emissions from the pipeline in the ultrasonic frequency range by means of at least one sound transducer, the output from which is an analogue electrical signal, (b) converting the analogue signal to a digital signal, and (c) analysing the digital signal to determine the characteristics of the slug flow.

By ultrasonic frequency range we mean frequencies above 15 KHz.

If necessary the analogue electrical signal can be amplified by use of a preamplifier. This provides the output capable of driving the signal through several hundred meters of cable.

Suitable transducers are those capable of operating in the ultrasonic frequency range, in particular in the range 20–200 KHz.

The transducer is suitably placed in direct contact with the external wall of the pipeline.

To ensure a good acoustic coupling between the transducer and the metal surface silicon grease or other suitable material may be used.

By detecting only those frequencies in the ultrasonic frequency range the measured emissions consist primarily of those transmitted through the pipe wall. In this way the background noise that would be transmitted through air would not be detected at the ultrasonic frequencies.

A Zener diode barrier may be present to ensure that the transducer and the preamplifier are protected from the mains voltage.

An average signal level device may be present to convert the high frequency AC signal to a DC voltage suitable for subsequent analysis.

Additional electronic filtering and amplification of the signal may be used to improve the signal to noise ratio.

The signal originating from the transducer is thus converted to a DC signal representing the average level across the frequency range.

This signal may be recorded by means of a plotter or may be stored and analysed using a suitable computer.

The characteristics of slug flow may be analysed as a function of time, in particular as a plot of time against amplitude of voltage.

The characteristics of slug flow which may be determined by the method of the present invention include the detection of slug propagation as distinct from wave propagation, the frequency of slugging and measurements of slug velocity and length.

The principal of slug detection by the method of the present invention relies on the emission of ultrasonic noise from the turbulence within the multiphase flow. Each flow regime has a characteristic time trace which allows the flow to be identified.

The trace observed in slug flow consists of a rapid rise from the background noise level to a maximum as the slug front passes the transducer often followed by an immediate decline. A steady, but higher than background, level is observed as the body of the slug passes, and then the signal finally decreases to the background level following the rear of the slug.

Such a characteristic trace is associated with the turbulence energy of the different parts of the slug.

Within a multiphase flow pipeline other events may also occur. Any events which consist of a variation in the local gas or liquid flowrates may be detected as a change in the signal level.

Such events may be observed as rapid changes in signal level associated with the propagation of non-slug events through the pipeline for example large amplitude waves or as slow changes in background level due to variations in the pipeline conditions for example line depressurisation following the discharge of a slug into the separator.

The large amplitude waves roll along the gas/liquid interface at a velocity less than the mixture velocity and do not bridge the pipeline whereas the slugs are pushed through the pipeline by the following gas bubble, have front velocities greater than the mixture velocity and do bridge the pipeline.

These properties and the characteristic time trace can be used to detect the presence of slugs in a multiphase pipeline and distinguish them from other events, in particular the large amplitude waves.

In order to measure the frequency of slugging a single transducer may be used. The frequency may be determined from the number of slugs passing the transducer in any given time period.

Improved measurements of the frequency of slugging and measurements of slug velocity and slug length may be made using a number of transducers each separated by short distances along the pipeline.

The preferred number of transducers is two positioned approximately 15-20 meters apart on the pipeline.

The slug velocity may be calculated from the distance between the two transducers divided by the time taken for the slug front to travel between them.

The slug velocity is given by the equation:

$$V = \frac{D}{Tsd - Tsu}$$

wherein
V = slug velocity
D = distance between the transducers
Tsd = time at which the slug front passes the downstream transducer
Tsu = time at which the slug front passes the upstream transducer.

The measured velocity of the slug may then be used to determine the slug length as the product of the measured velocity and the duration of the recorded slug trace.

The preferred method is to average the duration for the two transducers and thus the slug length may be given by the equation:

$$L = V\left[\frac{(Teu - Tsu) + (Ted - Tsd)}{2}\right]$$

wherein
IL = slug length
V = slug velocity
Teu = time at which the end of the slug passes the upstream transducer
Tsu = time at which the slug front passes the upstream transducer
Ted = time at which the end of the slug passes the downstream transducer
Tsd = time at which the slug front passes the downstream transducer.

In some situations the sharp decline in signal level at the rear of a slug is small and thus slugs may be misinterpreted as waves. In order to improve the differentiation between the events the velocity and length determined from the observed trace may be compared with the expected velocity and length for the event. In this way a pattern recognition system may be set up which allows for slugs and waves to be distinguished from one another on the basis of their velocity and length.

Such a recognition approach allows an operator to monitor the flow in a multiphase pipeline without the need for a background knowledge of multiphase flow hydrodynamics. It also automates the process of data analysis allowing large quantities of data to be reduced with the minimum effort.

The method of the present invention is suitable for analysing slug characteristics from any multiphase flow pipeline but is particularly suitable for pipeline flow comprising oil, gas and water.

The invention is further illustrated with reference to the accompanying Figures.

FIG. 1 is a schematic diagram of apparatus for use in the method according to the present invention. FIGS. 2-5 represent plots of amplitude of voltage against time which illustrate how the method of the present invention may be used to characterise slug flow. The amplitude of voltage is represented in terms of the output from the analogue-digital converter.

In FIG. 1 a resonant piezoelectric acoustic emission transducer (1) is positioned in contact with the outside of a multiphase flow pipeline (2). The transducer converts the ultrasonic acoustic emission signal received from the pipeline to an electrical signal. This signal then passes to the preamplifier (3) typically with 34 dB fixed gain. This amplifies the signal and provides an output capable of driving the signal through possibly several hundred meters of 50 ohm co-axial cable.

For intrinsic safety requirements the signal passes through a Zener barrier (4) which clamps the supply voltage (under fault conditions) transmitted through the preamplifier cable in the hazardous area. A line driver (5) provides an additional 6 dB of gain to the signal before the high frequency signal is converted to a DC voltage by the average signal level device (7).

A power supply module (6) provides a 15 V DC power supply to the system. The module (6) supplies power to the preamplifier (3) through the 50 ohm cable. The AC signal from the preamplier is transmitted through the same cable and decoupled within the power supply module(6).

The signal from the average signal level device (7) is digitised by the analogue-digital converter (ADC) (8) before being stored and analysed by means of the computer (9).

For convenience the Zener barrier, line driver, average signal level device and power supply module may be positioned within the same housing. In a similar way the ADC and computer may be a single component.

FIGS. 2-5 represent traces observed during monitoring various multiphase flowlines, containing oil, gas and water, in the North Slope fields in Alaska.

In FIG. 2 a flowline of 3200 m in length and 30 cms diameter was studied using a single 70 KHz transducer situated approximately 200 m from the manifold and separator at the end of the line. The transducer was positioned in direct contact with the external wall of the pipe with silicon grease used to ensure good acoustic coupling between the transducer and the metal. The signal from the transducer was amplified and transmitted to a signal processing and analysis unit situated approximately 100 m from the flowline.

The trace observed represents a slug passing the transducer. The sharp rise from the background level followed by the immediate decline is observed at (a) as the slug front passes the transducer. A steady but higher than background level is observed as the body of the slug passes and then the signal finally decreases at (b) as the rear of the slug passes the transducer. A slightly higher than background noise is observed at (c) which represents the signal due to gas depressurisation as the slug subsequently leaves the flowline.

FIG. 3 represents the trace observed on a 2000 m flowline with a 40 cm diameter using again a single 70 KHz transducer positioned approximately 200 m from the end of the line. A slug is again clearly observed at (b) and (c) which represent the start and end of the slug respectively. A shorter duration event is observed at (a)–(d) representing the passage of a large amplitude wave.

Figure 4:
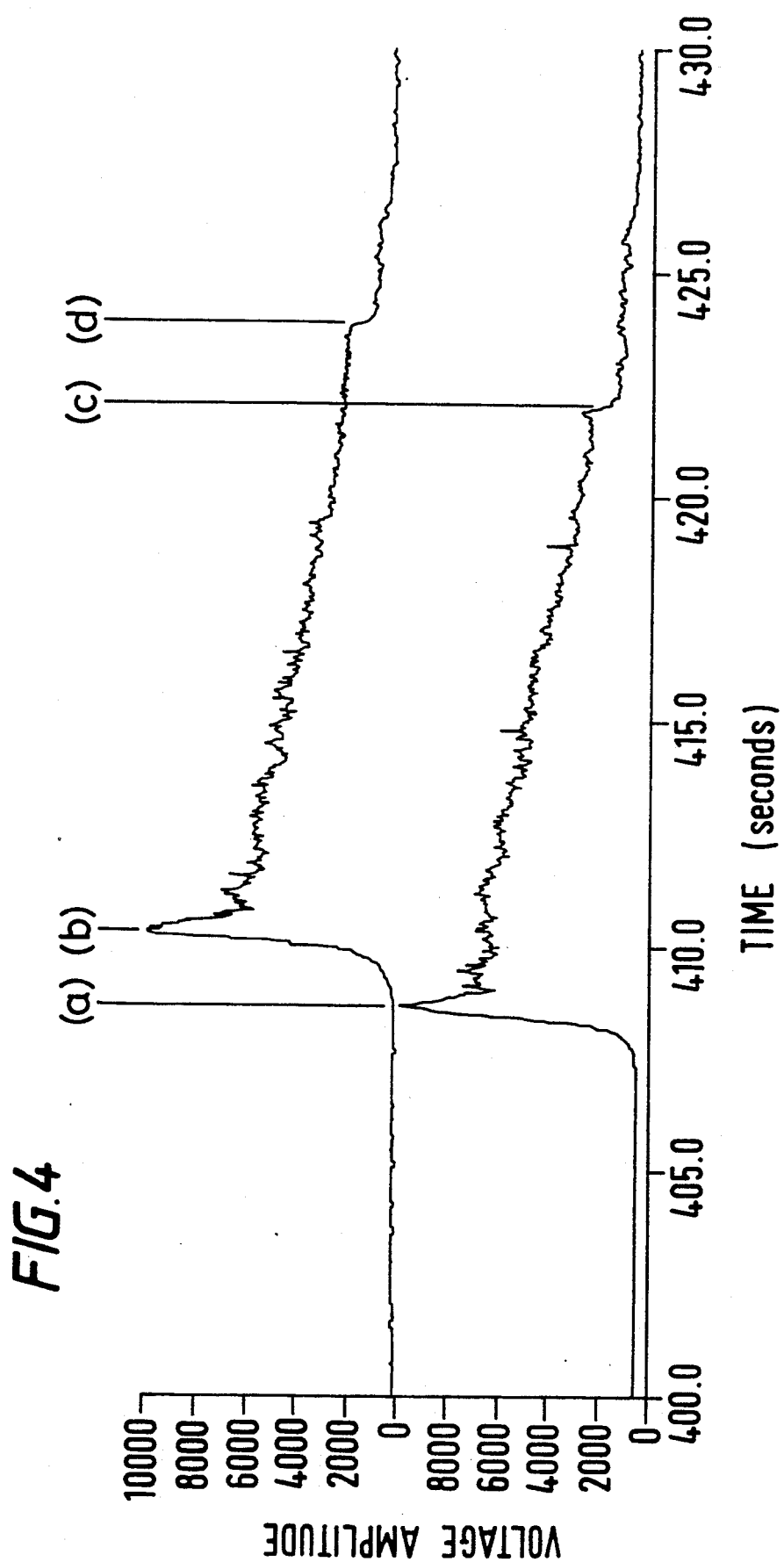

FIG. 4 represents the traces observed on a 8000 m flowline with 60 cm diameter using two transducers positioned approximately 18 m apart in a region 200 m from the end of the line. The upper trace represents the downstream transducer and the lower trace the upstream transducer. The start of the slug as it passes each transducer is observed at (a) and (b) repectively, the end of the slug being similarly observed at (c) and (d). From these traces the velocity and length of the slug may be determined using the formulae described above.

Figure 5:
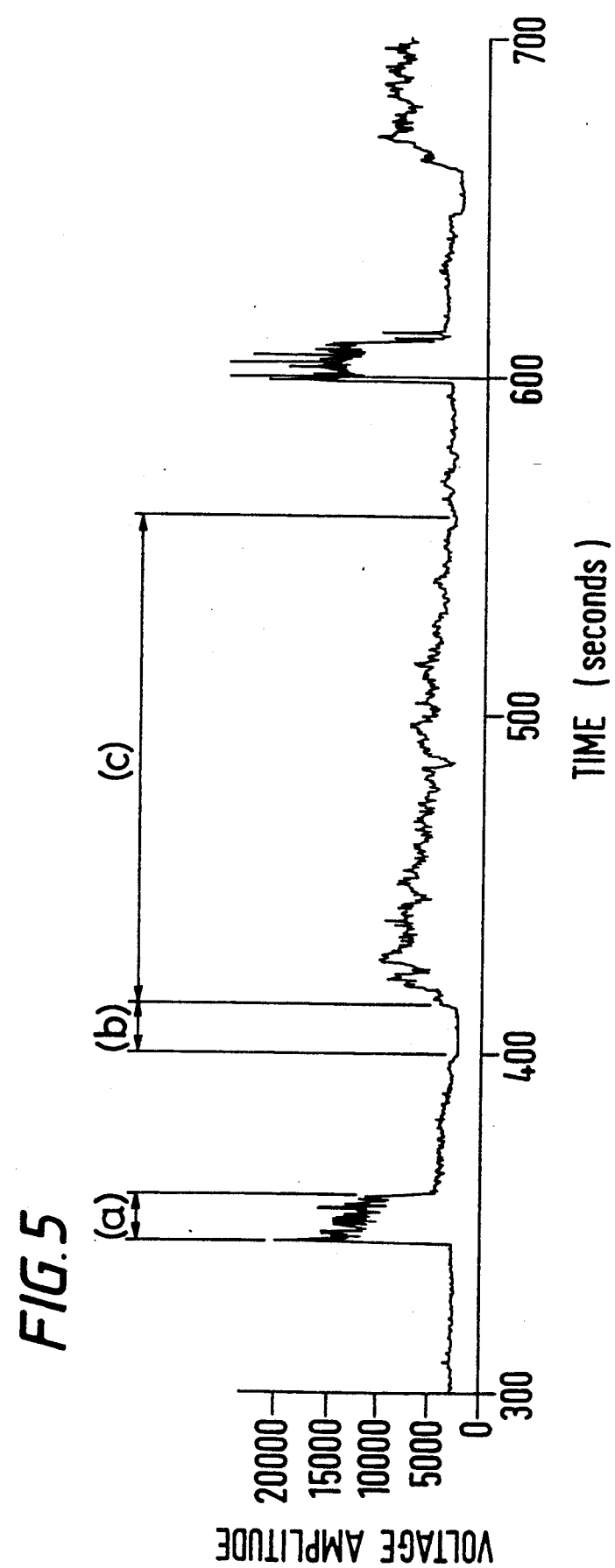

FIG. 5 represents the traces observed on a 10200 m flowline with a 60 cm diameter using a single transducer positioned approximately 300 m form the end of the line.

A slug is clearly observed at (a). As the slug enters the separator at the end of the line a stalling of the flow is seen at (b). This is followed by gas depressurisation at (c) following the exit of the slug from the flowline.

We claim:

1. A non-intrusive method for the determination of characteristics of slug flow in a multiphase flow pipeline wherein the method comprises the steps of:
   (a) detecting the acoustic emissions from the pipeline in the ultrasonic frequency range by means of at least one sound transducer, the output from which is an analogue electrical signal, wherein the transducer is in direct contact with the external wall of the pipeline,
   (b) converting the analogue signal to a digital signal, and
   (c) analyzing the digital signal to determine the characteristics of the slug flow.

2. A method according to claim 1 wherein the characteristic is selected from the group consisting of the detection of slug flow, the velocity of the slugs, the length of slugs or the frequency of slugging.

3. A method according to claim 1 wherein the multiphase flow comprises oil, gas and water.

4. A method according to claim 1 wherein the analogue electric signal is amplified.

5. A method according to claim 1 wherein the number of transducers is two.

6. A method according to claim 1 wherein the digital signal is analyzed as a function of time.

7. A method according to claim 6 wherein the digital signal is analyzed as a function of amplitude of voltage against time.

8. A non-intrusive method for the determination of characteristics of slug flow in a multiphase flow pipeline wherein the method comprises the steps of:
   (a) detecting the acoustic emissions from the pipeline in the ultrasonic frequency range by means of at least one sound transducer, the output from which is an analogue electrical signal, wherein the transducers are in direct contact with the external wall of the pipeline,
   (b) converting the analogue signal to a digital signal, and
   (c) analyzing the digital signal to determine the characteristics of the slug flow by a pattern recognition system for analyzing the digital signal.

* * * * *